United States Patent [19]

Liu et al.

[11] Patent Number: 4,672,033
[45] Date of Patent: Jun. 9, 1987

[54] ANTIBIOTICS X-14889 A,C AND D

[75] Inventors: Chao-Min Liu; John Westley, both of Cedar Grove, N.J.

[73] Assignee: Hoffmann-La Roche Inc., Nutley, N.J.

[21] Appl. No.: 737,120

[22] Filed: May 23, 1985

Related U.S. Application Data

[62] Division of Ser. No. 554,506, Nov. 23, 1983, Pat. No. 4,537,956.

[51] Int. Cl.$^4$ .................. C12P 19/60; C12P 17/18; C12P 1/06; C12R 1/465; C12R 1/60
[52] U.S. Cl. .................. 435/75; 435/119; 435/169; 435/886; 435/905
[58] Field of Search .................. 435/75, 119, 169

[56] References Cited

U.S. PATENT DOCUMENTS

| | | | |
|---|---|---|---|
| 4,161,520 | 7/1979 | Osborne et al. | 424/115 |
| 4,174,404 | 11/1979 | Nakatsukasa et al. | 424/283 |
| 4,368,265 | 1/1983 | Liu et al. | 435/75 |
| 4,407,946 | 10/1983 | Labeda et al. | 435/75 |
| 4,601,984 | 7/1986 | Liu et al. | 435/119 |

OTHER PUBLICATIONS

Journal of Antibiotics, vol. 30, No. 2, pp. 186–188, Feb. 1977.

Primary Examiner—Lionel M. Shapiro
Attorney, Agent, or Firm—Jon S. Saxe; Bernard S. Leon; Richard J. Mazza

[57] ABSTRACT

There is presented antibiotic compounds designated as Antibiotics X-14889 A, C and D of the formulas

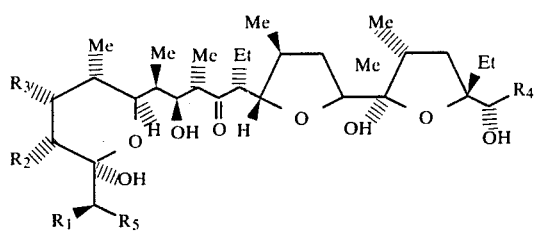

wherein (for X-14889A) $R_1$ is methyl, $R_2$ is methyl, $R_3$ is hydrogen, $R_4$ is methyl and $R_5$ is hydrogen or (for X-14889C) $R_1$ is hydrogen, $R_2$ is methyl, $R_3$ is hydrogen, $R_4$ is methyl and $R_5$ is $CO_2H$ or

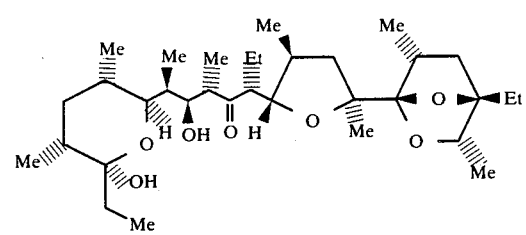

and the pharmaceutically acceptable salts thereof.

The compounds exhibit antimicrobial activity and one of the compounds X-14889C also exhibits activity against *Treponema hyodysenteriae* (in vitro), *Plasmodium berghei* and as food efficiency enhancers in ruminants.

Also presented is a process to produce the above compounds and another known component Antibiotic X-14889B.

1 Claim, No Drawings

ANTIBIOTICS X-14889 A,C AND D

This is a division of application Ser. No. 554,506 filed Nov. 23, 1983, now U.S. Pat. No. 4,537,956, issued Aug. 27, 1985.

DESCRIPTION OF THE INVENTION

The present invention relates to group of antibiotics which are of the formulas

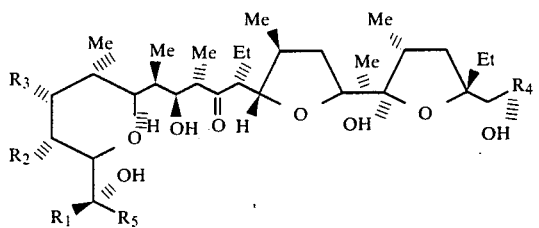

wherein (for X-14889A) $R_1$ is methyl, $R_2$ is methyl, $R_3$ is hydrogen, $R_4$ is methyl and $R_5$ is hydrogen or (for X-14889C) $R_1$ is hydrogen, $R_2$ is methyl, $R_3$ is hydrogen, $R_4$ is methyl and $R_5$ is $CO_2H$, or

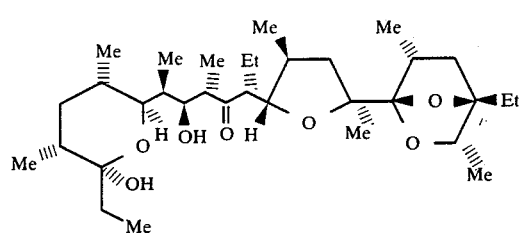

and the pharmaceutically acceptable salts thereof.

There are further provided according to the present invention a fermentation process for the production of such antibiotic substance together with the isolation techniques utilized to recover the compounds of Formulas I and II from the fermentation broth.

The organism producing the compounds of Formulas I and II is a new species designated Streptomyces sp. X-14889. A culture of the living organism given the laboratory designation X-14889 has been deposited at the U.S. Department of Agriculture, Agricultural Research Service, Northern Regional Research Laboratories, Peoria, Ill. and added to its collection of microorganisms as NRRL 15517. The culture most closely resembles *Streptomyces sparsogenes*.

A representative strain of Streptomyces X-14889 has the following characteristics:

Microscopic and Chemical Characteristics

Culture X-14889 grows in agar media of various compositions giving a type of growth characteristic of many aerobic actinomycetes. A substrate mycelium penetrates into the agar and remains unfragmented, while part of the aerial mass of growth differentiates into chains of spores. The chains are open to tight spirals and include more than 10 spores per chain. The spores are spiny and their average dimensions are 0.65×0.91 μm.

Chromatographic analysis of whole cell hydrolyzates revealed the presence of LL-diaminopimelic acid which, in addition to the properties listed above, suggests the assignment of strain X-14889 to the genus Streptomyces.

Macroscopic Characteristics

The characteristics of growth in different agar media are summarized in Table 1 below. The data were recorded after 14 days of incubation at 28° C.

TABLE 1

| Medium | Amount of growth and degree of sporulation | Color of the aerial mass (1) | Color of the reverse mycelium (1) |
|---|---|---|---|
| Yeast-malt extract (ISP-2) | abundant growth; waxy appearance; no sporulation | luggage tan (4 pg) | luggage tan (4 pg) |
| Oatmeal agar (ISP-3) | abundant growth; good sporulation | ashes (5 fe) | gray (g), mixed with tan (3 gc) |
| Inorganic salts-starch agar (ISP-4) | abundant growth; no sporulation | oak brown (4 pi) | light brown (4 ng) |
| Glycerol-asparagine agar (ISP-5) | poor growth; no sporulation | light gray (c) | light gray (c) |

(1) The color code is that of the Color Harmony Manual, 4th edition, Container Corporation of America, 1958.

Physiological Characteristics

Culture X-14889 can grow at the expense of glucose, galactose, fructose, arabinose, rhamnose, mannitol, sucrose and raffinose. There is no growth on xylose, inositol or cellulose, and slight or doubtful growth on salicin. Growth is inhibited by streptomycin. Melanin production in ISP-7 medium, $H_2S$ production in ISP-6 medium, and nitrate reduction in ISP-8 medium are negative. Gelatin and casein are hydrolyzed but starch is not. The NaCl tolerance is low (less than 2%).

Taxonomic Conclusions

The phenotypic characters listed above for culture X-14889 allow the assignment of this culture to a group of Streptomyces species which have a marked resemblance with the strain under study according to phenotypic data reported in the literature, i.e.,

[Buchanan, R. E. and N. E. Gibbons. 1974. Bergey's Manual of Determinative Bacteriology, 8th edition. Williams and Wilkins Co., Baltimore.

Shirling, E. B. and D. Gottlieb. 1968. Cooperative description of type cultures of Streptomyces. II. Species descriptions from first study. Int. J. Syst. Bacteriol. 18: 69–189.

Shirling, E. B. and D. Gottlieb. 1968. Cooperative description of type cultures of Streptomyces. III. Additional species descriptions from first and second studies. Int. J. Syst. Bacteriol. 18: 279–392.

Shirling, E. B. and D. Gottlieb. 1969. Cooperative description of type strains of Streptomyces. IV. Species descriptions from the second, third and fourth studies. Int. J. Syst. Bacteriol. 19: 391–512.

Shirling, E. B. and D. Gottlieb. 1972. Cooperative description of type strains of Streptomyces. V. Additional descriptions. Int. J. Syst. Bacteriol. 22: 265–394.]

The species are *S. albaduncus, S. canus, S. cuspidosporus, S. olivoviridis, S. craterifer, S. saraceticus* and *S. sparsogenes. S. albaduncus* differs from X-14889 in the utilization of xylose, inositol and sucrose; *S. canus* utilizes xylose and inositol; *S. cuspidosporus* grows on xylose, inositol and salicin; *S. olivoviridis* is negative on raffinose and sucrose and is positive on xylose; *S. craterifer* utilizes xylose and the utilization of sucrose and raffinose is doubtful; *S. saraceticus* utilizes xylose, but the utilization of rhamnose is doubtful. *S. sparsogenes* is perhaps the species that more closely resembles X-14889. Neither organism sporulates well on selected media, and the utilization of sugars is similar with the exception of xylose, which is utilized by *S. sparsogenes*, and of galactose, for which this species is negative. Other differences include the fact that the individual spores in the spore chains of *S. sparsogenes* are indistinct, which suggests the presence of a sheath and the hygroscopic character of the spore mass. In summary, even though X-14889 resembles several other species of Streptomyces, the production of unique antibiotics and several physiological and morphological characteristics set it apart from all other species with which it has been compared.

The species Streptomyces X-14889 described herein includes all strains of Streptomyces which form the compounds of Formulas I and II and which cannot be definitely differentiated from the culture number X-14889 and its subcultures including mutants and variants. The compounds of Formulas I and II are identified herein and after this identification is known, it is easy to differentiate the strains producing Formula I and II compounds from others.

Streptomyces sp. X-14889, when grown under suitable conditions, produces compounds of Formulas I and II. A fermentation broth containing Streptomyces sp. X-14889 is prepared by inoculating spores or mycelia of the organism producing the compounds of Formulas I and II into a suitable medium and then cultivating under aerobic conditions. For the production of compounds of the Formulas I and II, cultivation on a solid medium is possible but for production in large quantities, cultivation in a liquid medium is preferable. The temperature of cultivation may be varied over a wide range, 20°–35° C., within which the organism may grow but a temperature of 26°–30° C. and a substantially neutral pH are preferred. In the submerged aerobic fermentation of the organism for the production of the compounds of Formulas I and II, the medium may contain as the source for carbon, a commercially available glyceride oil or a carbohydrate such a glycerol, glucose, maltose, lactose, dextrin, starch, etc. in pure or crude states and as the source of nitrogen, an organic material such as soybean meal, distillers' solubles, peanut meal, cotton seed meal, meat extract, peptone, fish meal, yeast extract, corn steep liquor, etc. and when desired inorganic sources of nitrogen such as nitrates and ammonium salts and mineral salts such as ammonium sulfate, magnesium sulfate and the like. It also may contain sodium chloride, potassium chloride, potassium phosphate and the like and buffering agents such as sodium citrate, calcium carbonate or phosphates and trace amounts of heavy metal salts. In aerated submerged culturing procedures, an anti-foam agent such as liquid paraffin, fatty oils or silicone compounds is used. More than one kind of carbon source, nitrogen source or anti-foam source may be used for production of the compounds of Formulas I and II.

The following Examples will serve to illustrate this invention without limiting it thereto.

EXAMPLE 1

Shake flask fermentation of Streptomyces X-14889

The X-14889 culture is grown and maintained on a starch-casein agar slant having the following composition (grams/liter distilled water):

| | |
|---|---|
| Soluble starch | 10.0 |
| Casein | 1.0 |
| $K_2HPO_4$ | 0.5 |
| $MgSO_4$ (anhydrous) | 0.5 |
| Agar | 20.0 |
| Adjust to pH 7.4 with NaOH before autoclaving. | |

The slant is inoculated with X-14889 culture and incubated at 28° C. for 10–14 days. A chunk of agar containing the sporulated culture from the agar slant is then used to inoculate a 500-ml Erlenmeyer flask containing 100 ml sterilized inoculum medium having the following composition (grams/liter tap water):

| | |
|---|---|
| Soylose 105 | 10.0 |
| Cerelose | 20.0 |
| $CaCO_3$ | 0.2 |
| $CoCl_3.6H_2O$ | 0.001 |
| $Na_2SO_4$ | 1.0 |
| pH to 6.0 before sterilization. | |

The inoculated flask is incubated at 28° C. for 72 hours on a rotary shaker, operating at 250 rpm with a 2-inch stroke. A 3-ml portion (3%, v/v) of the resulting culture is then used to inoculate a 500-ml Erlenmeyer flask containing 100 ml sterilized production medium having the same composition as the inoculum medium. The inoculated flask is incubated at 28° C. for 6 days on a rotary shaker running at 250 rpm with a 2-inch stroke.

EXAMPLE 2

Tank fermentation of Streptomyces X-14889

The X-14889 culture is grown and maintained on a starch-casein agar slant as described in Example 1. A chunk of agar containing the sporulated culture from the agar slant is then used to inoculate a 6-liter Erlenmeyer flask containing 2 liters of medium having the following composition (in grams/liter tap water):

| | |
|---|---|
| Soylose 105 | 10.0 |
| Cerelose | 20.0 |
| $CaCO_3$ | 0.2 |
| $CoCl_2.6H_2O$ | 0.001 |
| $Na_2SO_4$ | 1.0 |
| pH to 6.0 before sterilization for 45 minutes in an autoclave. | |

The inoculated flask is incubated at 28° C. for 5 days on a rotary shaker operating at 250 rpm with a 2-inch stroke. Four liters of the resulting culture is used as inoculum to start a fermentation in a 100-gallon fermentor containing 60 gallons of medium having the following composition (grams/liter tap water):

| | |
|---|---|
| Soylose 105 | 10.0 |
| Cerelose | 20.0 |
| $CaCO_3$ | 0.2 |
| $CoCl_2.6H_2O$ | 1.0 |
| Sag 4130 Antifoam (Union Carbide) | 0.1 |
| pH to 6.0 before sterilization for 45 minutes with a 15 lb/in² steam. | |

The inoculated medium is aerated with compressed air at a rate of 3 cubic feet per minute and is stirred with agitators at 280 rpm. The fermentation is carried out at 28° C. for 72 hours. Twenty gallons of the resulting culture are then used to inoculate a 500-gallon fermentor containing 360 gallons of medium with the following composition (grams/liter tap water):

| | |
|---|---|
| Soylose 105 | 10.0 |
| Cerelose | 20.0 |
| CaCO$_3$ | 0.2 |
| CoCl$_2$6H$_2$O | 0.001 |
| Na$_2$SO$_4$ | 1.0 |
| Sag 4130 Antifoam (Union Carbide) | 0.1 |
| pH to 6.0 before sterilization for 45 minutes with a 15 lb/in$^2$ steam. | |

The inoculated fermentor is aerated with compressed air at 20 cubic feet per minute and is stirred with agitators at 280 rpm. The fermentation is carried out at 28° C. for 139 hours.

EXAMPLE 3

Isolation of Antibiotix X-14889A from tank fermentation of Streptomyces culture X-14889

The whole broth (360 gallons, 1368 liters) from the 139 hour fermentation of Streptomyces culture sp. X-14889 was extracted twice with equal volumes of ethyl acetate at the harvest pH (7.1). The solvent layer was separated and concentrated under reduced pressure to an oil. The oil was dissolved in n-hexane and extracted twice with equal volumes of acetonitrile. The extracted hexane phase was concentrated under reduced pressure to an oil (70 g), dissolved in 1.5 liters of methylene chloride, and washed sequentially with 0.5 liters of 1N HCl, water, saturated sodium carbonate and water. The solvent layer was dried over sodium sulfate and concentrated under reduced pressure. This concentrate was chromatographed on a methylene chloride slurry-packed 800 g silica gel (Davison grade 62) column. The column was eluted with 4 liters of methylene chloride, followed by 4 liters diethyl ether-hexane (9:1). Fractions of 40 ml each were collected, and fraction numbers 60–120 were pooled and concentrated under reduced pressure to an oil (6 g). The oil was dissolved in minimum volume of methylene chloride and was chromatographed on a methylene chloride slurry-packed 300 g silica gel (Davison grade 62) column. The column was eluted with 2-liters methylene chloride and then a gradient between 4 liters of diethyl ether-n-hexane-acetone-ammonium hydroxide (7:3:1:0.02) and 4 liters of diethyl ether-acetone (9:1). Fractions of 25 ml each were collected. Fraction numbers 54–64 were pooled, solvent removed under reduced pressure and the residue was redissolved in ethyl acetate and sequentially washed with 1N HCl, water, saturated sodium carbonate and water and dried over sodium sulfate. Solvent was removed under reduced pressure and the residue was crystallized from n-hexane, yielding antibiotic X-14889A.

mp. 149°–150° C., $[\alpha]_D^{25} = +29.3°$ C. (cl in MeOH), +16.7° C. (cl in CHCl$_3$).

Microanalysis calcd. for C$_{33}$H$_{60}$O$_8$ (584.84):

Calcd.: %C, 67.77; %H, 10.34. Found: %C, 67.78; %H 10.50.

Structure was established by $^{13}$C NMR (antibiotic X-14889A = descarboxy antibiotic X-14889B). Antibiotic X-14889A is active in vitro against gram positive microorganisms. MIC: 6.25–1.57 mcg/ml.

EXAMPLE 4

Isolation of Antibiotic X-14889B-sodium salt from tank fermentation

From the same column that antibiotic X-14889A was isolated from fractions 54–64 (see Example 3), fractions 124–200 were processed by the same steps as described in Example 3. Crystallization from diethyl ether by the addition of hexane yielded antibiotic X-14889B-sodium salt as a hemihydrate.

mp. 139°–140° C., $[\alpha]_D^{25} = 5.9°$ C. (cl in MeOH), 7.4° C. (cl in CHCl$_3$).

Microanalysis calcd. for C$_{34}$H$_{59}$O$_{10}$Na.½H$_2$O (659.84):

Calcd.: %C, 61.89; %H, 9.17; %Na, 3.48; %H$_2$O, 1.37. Found: %C, 61.92; %H, 9.27; %Na, 3.55; %H$_2$O, 1.71.

Structure of antibiotic X-14889B was determined by X-ray analysis of its thallium salt (antibiotic X-14889B is an isomer of the known antibiotic Lysocellin). Antibiotic X-14889B-Na salt is active in vitro against gram positive microorganisms. MIC: 6.25–0.09 mcg/ml.

EXAMPLE 5

Isolation of Antibiotic X-14889C-sodium salt

From the same column that antibiotic X-14889A and -B were isolated (see Examples 3 and 4), fractions 251–300 yielded antibiotic X-14889C-sodium salt via the procedure described in Example 3. Antibiotic X-14889C-sodium salt crystallized from diethyl ether by the addition of hexane, as the monohydrate.

mp. 139°–141° C., $[\alpha]_D^{25} = 19.3°$ C. (cl in CHCl$_3$).

Microanalysis calcd. for C$_{33}$H$_{57}$O$_{10}$Na.H$_2$O (654.82):

Calcd.: %C, 60.53; %H, 9.08; %Na, 3.51; %H$_2$O, 2.75. Found: %C, 60.99, 61.24; %H, 9.16, 8.79; %Na, 3.68; %H$_2$O, 2.00.

Structure was determined by X-ray crystallography (antibiotic X-14889C is a lower homologue of Lysocellin).

EXAMPLE 6

Isolation of Antibiotic X-14889D

Rechromatography of the mother liquor of antibiotic X-14889C on a methylene chloride slurry-packed 30 g silica gel (Davison grade 62) column, eluted with 400 ml methylene chloride, followed by 400 ml diethyl ether-hexane (1:1), yielded antibiotic X-14889D (anhydro antibiotic X-14889A).

mp. 117° C.

Microanalysis calcd. for C$_{33}$H$_{58}$O$_7$ (566.82):

Calcd.: %C, 69.93; %H, 10.31 Found: %C, 69.60, 69.87; %H, 10.36, 10.28.

Structure was determined by X-ray crystallography.

Antibiotics X-14889, A, C and D exhibit antimicrobial activity against a variety of organisms as indicated in the table below.

| *In vitro Microorganism | Minimal inhibitory concentration (mcg/ml) | | |
|---|---|---|---|
| | X-14889A | X-14889C | X-14889D |
| G(+) cocci | | | |
| Streptococcus faecium ATCC 8043 | 1.57 | 0.08 | 125 |
| Staphylococcus aureus ATCC 6538P | 6.25 | 5 | 125 |
| Micrococcus luteus ATCC 9341 | 6.25 | 5 | |
| G(+) rods | | | |

-continued

| *In vitro Microorganism | Minimal inhibitory concentration (mcg/ml) | | |
|---|---|---|---|
| | X-14889A | X-14889C | X-14889D |
| Bacillus megaterium ATCC 8011 | 6.25 | 2.5 | 1000 |
| Bacillus sp. E ATCC 27359 | 3.13 | 0.63 | 7.9 |
| Bacillus subtilis ATCC 558 | 3.13 | 1.25 | 1000 |
| Bacillus sp. TA ATCC 27860 G(+) filaments | 3.13 | 1.25 | 1000 |
| Mycobacterium phlei ATCC 355 | 100 | 50 | 1000 |
| Streptomyces cellulosae ATCC 3313 | 100 | 10 | 1000 |
| Molds | | | |
| Paecilomyces varioti ATCC 28820 | 100 | 125 | 1000 |
| Penicillium digitatum ATCC 26821 | 100 | 250 | 1000 |
| Yeasts | | | |
| Candida albicans NRRL 477 | 100 | 62.5 | 1000 |
| Saccharomyces cerevisiae ATCC 4226 | 100 | 500 | 1000 |

*As determined by an agar diffusion well method.

As indicated above the antibiotics of the present invention and salts thereof possess the property of adversely affecting the growth of certain gram positive bacteria. They are useful in wash solutions for sanitary purposes as in the washing of hands and the cleaning of equipment, floors or furnishings of contaminated rooms or laboratories.

When utilized as a disinfectent one skilled in the art should take into account the minimum inhibitory concentration of the particular antibiotic in computing the concentration of antibiotic to apply against the target organism.

Antibiotic X-14889C also exhibits the following activities:

(A) Activity against swine dysentery

Antiobiotic X-14889C sodium salt exhibits in vitro activity against *Treponema hyodysenteriae,* a causative agent in swine dysentery exhibiting activity at 5 mcg/ml.

Testing for activity against *Treponema hyodysenteriae,* a cause of swine dysentery, consisted of inoculation of blood agar plates containing a series of two fourfold dilutions of the antibiotic and ipronidazole, an agent effective against swine dysentery, with tenfold dilutions of each of the *T. hyodysenteriae* strains (H 78, H 140, H 179). After 48 hours of incubation at 42° C. in an anerobic atmosphere, Minimum Inhibitory Concentrations were recorded as the lowest concentrations of compound which completely inhibited the most dilute inoculum of each *T. hyodysenteriae* strain.

(B) Activity against Plasmodium berghei

Antibiotic X-14889C sodium salt exhibits in vitro activity against Plasmodium berghei at a subcutaneous dose of 22 mg/kg.

(C) Activity as a feed efficiency enhancer in animals

Antibiotic X-14889C sodium salt exhibits in vitro activity as a feed efficiency enhancer in ruminants. At 50 ppm the antibiotic the percentage of Total Volatile Fatty Acids was 154.3% versus 100% for control in the standard fisticulated ruminent model.

Based on the in vitro results above it may be hypothsized that administration of antibiotic X-14889C hereafter "Antibiotic" or "Antibiotic Compound" prevents and treats ketosis as well as improves feed utilization in ruminants or swine. The causative mechanism of ketosis is a deficient production of propionate compounds. A presently recommended treatment is administration of propionic acid or feeds which preferentially produce propionates. It is obvious that encouraging propionate production from ordinary feeds will reduce incidence of ketosis.

Based on the in vitro results it would be predictable that antibiotic X-14889C increases the efficiency of feed utilization in ruminant animals when it is administered orally to the animals. The easiest way to administer the antibiotic is by mixing it in the animal's feed.

However, the antibiotic can be usefully administered in other ways. For example, it can be incorporated into tablets, drenches, boluses, or capsules, and dosed to the animals. Formulation of the antibiotic compound in such dosage forms can be accomplished by means of methods well known in the veterinary pharmaceutical art.

Capsules are readily produced by filling gelatin capsules with any desired form of the desired antibiotic. If desired, the antibiotic can be diluted with an inert powdered diluent, such as a sugar, starch, or purified crystaline cellulose in order to increase its volume for convenience in filling capsules.

Tablets of the antibiotic are made by conventional pharmaceutical processes. Manufacture of tablets is a well-known and highly advanced art. In addition to the active ingredient, a tablet usually contains a base, a disintegrator, an absorbent, a binder, and a lubricant. Typical bases include lactose, fine icing sugar, sodium chloride, starch and mannitol. Starch is also a good disintegrator as is alginic acid. Surface active agents such as sodium lauryl sulfate and dioctyl sodium sulphosuccinate are also sometimes used.

Commonly used absorbents again include starch and lactose while magnesium carbonate is also useful for oily substance. Frequently used binders are gelatin, gums, starch, dextrin and various cellulose derivatives. Among the commonly used lubricants are magnesium stearate, talc, paraffin wax, various metallic soaps, and polyethylene glycol.

The administration of the antibiotic compound may be as a slow-pay-out bolus. Such boluses are made as tablets except that a means to delay the dissolution of the antibiotic is provided. Boluses are made to release for lengthy periods. The slow dissolution is assisted by choosing a highly water-insoluble form of the antibiotic. A substance such as iron filing is added to raise the density of the bolus and keep it static on the bottom of the rumen.

Dissolution of the antibiotic is delayed by use of a matrix of insoluble materials in which the drug is imbedded. For example, substances such as vegetable waxes, purified mineral waxes, and water-insoluble polymeric materials are useful.

Drenches of the antibiotic are prepared most easily by choosing a water-soluble form of the antibiotic. If an insoluble form is desired for some reason, a suspension may be made. Alternatively, a drench may be formulated as a solution in a physiologically acceptable solvent such as a polyethylene glycol.

Suspensions of insoluble forms of the antibiotic can be prepared in nonsolvents such as vegetable oils such as peanut, corn, or sesame oil, in a glycol such as propylene glycol or a polyether glycol; or in water, depending on the form of the antibiotic chosen.

Suitable physiologically acceptable adjuvants are necessary in order to keep the antibiotic suspended. The adjuvants can be chosen from among the thickeners, such as carboxymethylcellulose, polyvinylpyrrolidone, gelatin, and the alginates. Many classes of surfactants serve to suspend the antibiotic. For example, lecithin, alkylphenol polyethylene oxide adducts, naphthalenesulfonates, alkylbenzesulfonates, and the polyoxyethylene sorbitan esters are useful for making suspensions in liquid nonsolvents.

In addition many substances which affect the hydrophilicity, density, and surface tension of the liquid can assist in making suspensions in individual cases. For example, silicone anti-foams, glycols sorbitol, and sugars can be useful suspending agents.

The suspendable antibiotic may be offered to the grower as a suspension, or as a dry mixture of the antibiotic and adjuvants to be diluted before use.

The antibiotic may also be administered in the drinking water of the ruminants. Incorporation into drinking water is performed by adding a water-soluble or water-suspendable form of the antibiotic to the water in the proper amount. Formulation of the antibiotic for addition to drinking water follows the same principles as formulation of drenches.

The most practical way to treat animals with the antibiotic compound is by the formulation of the compound into the feed supply. Any type of feed may be medicated with the antibiotic compounds, including common dry feeds, liquid feeds, and pelleted feeds.

The methods of formulating drugs into animal feeds are well-known. It is usual to make a concentrated drug premix as a raw material for medicated feeds. For example, typical drug premixes may contain from about one to about 400 grams of drug per pound of premix. The wide range results from the wide range of concentration of drug which may be desired in the final feed. Premixes may be either liquid or solid.

The formulation of ruminant feeds containing the proper amounts of antibiotic for useful treatment is well understood. It is necessary only to calculate the amount of compound which it is desired to administer to each animal, to take into account the amount of feed per day which the animal eats and the concentration of antibiotic compound in the premix to be used, and calculate the proper concentration of antibiotic compound, or of premix, in the feed.

All of the methods of formulating, mixing and pelleting feeds which are normally used in the ruminant feed art are entirely appropriate for manufacturing feeds containing the antibiotic compound.

As predicated on in vitro results, oral administration of the antibiotic beneficially alters the production of propionates relative to the production of acetates in the rumen. It may therefore be postulated that the same treatment would also benefit monogastric animals which ferment fibrous vegetable matter in the cecum since it would be expected that a beneficial change in the propionate/acetate ration would occur upon oral administration of the instant antibiotic. Horses, swine and rabbits are exemplary animals which digest a part of their food by cecal fermentation.

The incorporation of Antibiotic X-14889C into any of the dosage forms outlined above should be accomplished taking into account the in vitro level of activity of 50 ppm noted above and the $LD_{50}$ of the compound noted below.

Antibiotic X-14889C has the following toxicity expressed as $LD_{50}$'s:

$LD_{50}(PO) = 190$ mg/kg $LD_{50}(1P) = 120$ mg/kg

Antibiotics X-14889 A, C and D are polyether antibiotics and form a variety of pharmaceutically acceptable salts. These salts are prepared from the free acid form of the particular antibiotic by methods well-known for compounds of the polyether type in the art; for example, by washing the free acid in solution with a suitable base or salt. Examples of such pharmaceutically acceptable basic substances capable of forming salts for the purpose of the present invention include alkali metal bases, such as sodium hydroxide, potassium hydroxide, lithium hydroxide and the like; alkaline earth metal bases, such as calcium hydroxide, barium hydroxide and the like; and ammonium hydroxide. Alkali metal or alkaline earth metal salts suitable for forming pharmaceutically acceptable salts can include anions such as carbonates, bicarbonates and sulfates.

Examples of organic bases forming pharmaceutically acceptable salts with the polyether compounds are lower alkyl amines, primary, secondary and tertiary hydroxy-lower alkylamines such as ethylamine, isopropylamine, diethylamine, methyl-n-butylamine, ethanolamine and diethanolamine.

An amine especially preferred is N-methylglucamine. Salts of N-methylglucamine are of special value because of their water-solubility which makes them amenable to parenteral use.

Antibiotic X-14889C also exhibits slight in vitro activity at 1 ppm as an anticoccidial agent against *Eimeria tenella*.

What is claimed is:

1. A process to produce antibiotics X-14889 A, B, C and D which comprises:
    cultivating a strain of Streptomyces X-14889, NRRL 15517 in an aqueous carbohydrate solution containing a nitrogenous nutrient under submerged aerobic conditions and thereafter isolating the X-14889 A, B, C and D antibiotics from said solution.

* * * * *